US009301532B2

(12) United States Patent
Assmann et al.

(10) Patent No.: US 9,301,532 B2
(45) Date of Patent: Apr. 5, 2016

(54) ACTIVE COMPOUND COMBINATIONS

(71) Applicant: Bayer Intellectual Property GmbH, Monheim (DE)

(72) Inventors: Lutz Assmann, Langenfeld (DE); Ulrike Wachendorff-Neumann, Neuwied (DE); Peter Dahmen, Neuss (DE); Heike Hungenberg, Langenfeld (DE); Wolfgang Thielert, Odenthal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/511,153

(22) Filed: Oct. 9, 2014

(65) Prior Publication Data

US 2015/0024937 A1 Jan. 22, 2015

Related U.S. Application Data

(62) Division of application No. 14/013,088, filed on Aug. 29, 2013, now Pat. No. 8,883,180, which is a division of application No. 12/742,753, filed as application No. PCT/EP2008/010107 on Nov. 28, 2008, now Pat. No. 8,546,305.

(30) Foreign Application Priority Data

Dec. 11, 2007 (EP) ..................... 07122950

(51) Int. Cl.
| *A01N 51/00* | (2006.01) |
| *A01N 43/56* | (2006.01) |
| *A01N 43/80* | (2006.01) |
| *A01N 43/54* | (2006.01) |
| *A01N 43/78* | (2006.01) |
| *A01N 43/88* | (2006.01) |

(52) U.S. Cl.
CPC ............... *A01N 51/00* (2013.01); *A01N 43/54* (2013.01); *A01N 43/56* (2013.01); *A01N 43/78* (2013.01); *A01N 43/80* (2013.01); *A01N 43/88* (2013.01)

(58) Field of Classification Search
CPC ....... A01N 51/00; A01N 43/54; A01N 43/56; A01N 43/78; A01N 43/80; A01N 43/88
See application file for complete search history.

(56) References Cited

U.S. PATENT DOCUMENTS

| 7,309,711 | B2 * | 12/2007 | Dahmen ................ A01N 43/80 514/341 |
| 7,696,355 | B2 | 4/2010 | Assmann et al. |
| 8,268,750 | B2 * | 9/2012 | Funke .................... A01N 43/56 504/130 |
| 8,546,305 | B2 | 10/2013 | Assmann et al. |
| 8,883,180 | B2 | 11/2014 | Assmann et al. |

| 2003/0018992 | A1 | 1/2003 | Asrar et al. |
| 2003/0186813 | A1 | 10/2003 | Pershing et al. |
| 2007/0060579 | A1 | 3/2007 | Wachendorff-Neumann et al. |
| 2009/0156592 | A1 | 6/2009 | Pasteris et al. |
| 2010/0197743 | A1 | 8/2010 | Münks et al. |
| 2010/0227900 | A1 | 9/2010 | Aβmann et al. |
| 2010/0240619 | A1 | 9/2010 | Gregory et al. |
| 2010/0248961 | A1 | 9/2010 | Assmann et al. |
| 2010/0311580 | A1 | 12/2010 | Assmann et al. |
| 2011/0033433 | A1 | 2/2011 | Davies et al. |
| 2011/0143935 | A1 | 6/2011 | Assmann et al. |
| 2011/0160052 | A1 | 6/2011 | Assmann et al. |

FOREIGN PATENT DOCUMENTS

| WO | WO 2005/009131 A1 | 2/2005 |
| WO | WO 2006/068669 A1 | 6/2006 |
| WO | WO 2006/108552 A2 | 10/2006 |
| WO | WO 2007/101541 A2 | 9/2007 |
| WO | WO 2008/034785 A2 | 3/2008 |
| WO | WO2008034785 A1 * | 3/2008 ............. A01N 43/56 |

OTHER PUBLICATIONS

International Search Report of International Application No. PCT/EP2008/010107, European Patent Office, Rijswijk, Netherlands, mailed Apr. 3, 2009.
"Prevent," Your Dictionary [online] [retrieved Feb. 28, 2013] Retrieved from the Internet: <URL: http://www.yourdictionary.com/Prevention>.
Office Action in U.S. Appl. No. 12/742,753, § 371(c) date: Aug. 23, 2010, inventors Assmann et al., mailed Jul. 16, 2012.
Office Action in U.S. Appl. No. 12/742,753, § 371(c) date: Aug. 23, 2010, inventors Assmann et al., mailed Mar. 5, 2013.
Office Action in U.S. Appl. No. 12/699,246, filed Feb. 3, 2010, Assmann et al., mailed Aug. 15, 2012.
Office Action in U.S. Appl. No. 12/699,246, filed Feb. 3, 2010, Assmann et al., mailed Jan. 14, 2013.
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DOX-A7881 and Clopyralid in Canola (*Brassica napus*)," *Weed Tech.* 3:690-695, The Weed Science Society of America, United States (1989).

(Continued)

*Primary Examiner* — Jane C Osweeki
(74) *Attorney, Agent, or Firm* — Sterne, Kessler, Goldstein & Fox PLLC

(57) ABSTRACT

The invention relates to active compound combinations, in particular a fungicidal and/or insecticidal composition, comprising Isotianil (3,4-dichloro-N-(2-cyanophenyl)-5-isothiazolecarboxamide) and at least one further insecticide of the anthranilamide group and optionally one further insecticide of the neonicotinoids. Moreover, the invention relates to a method for curatively or preventively controlling the phytopathogenic fungi and/or microorganisms and/or pests of plants or crops, to the use of a combination according to the invention for the treatment of seed, to a method for protecting a seed and not at least to the treated seed.

9 Claims, No Drawings

(56) References Cited

OTHER PUBLICATIONS

Blackshaw, R.E., et al., "Herbicide Combinations for Postemergent Weed Control in Safflower (*Carthatnzis tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

Colby, S.R., "Calculating Synergistic and Antagonistic Responses of Herbicide Combinations," *Weeds* 15:20-22, Weed Society of America, United States (1967).

Flint, J.L., et al., "Analyzing Herbicide Interactions: A Statistical Treatment of Colby's Method," *Weed Tech.* 2:304-309, The Weed Science Society of America, United States (1988).

Gillespie, G.R. and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, K.N. and O'Sullivan, A., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," Weed Science 23:4-6, The Weed Science Society of America, United States (1975).

Salzman, F.P. and Renner, K.A.,"Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G., and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

\* cited by examiner

ACTIVE COMPOUND COMBINATIONS

The invention relates to active compound combinations, in particular a fungicidal and/or insecticidal composition, comprising Isotianil (3,4-dichloro-N-(2-cyanophenyl)-5-isothiazolecarboxamide, CAS No 224049-04-1) and at least one further insecticide of the anthranilamide group and optionally one further insecticide of the neonicotinoids.

Moreover, the invention relates to a method for curatively or preventively controlling the phytopathogenic fungi and/or microorganisms and/or pests of plants or crops, to the use of a combination according to the invention for the treatment of seed, to a method for protecting a seed and not at least to the treated seed.

It is already known that the compound (A) Isotianil has fungicidal and insecticidal properties. In addition, it has also been found that the isothiazolecarboxylic acid derivatives are highly suitable for protecting plants against attack by undesirable phytopathogenic fungi and microorganisms (U.S. Pat. No. 5,240,951 und JP-A 06-09313). The compound (A) Isotianil according to the invention is suitable both for mobilizing the defenses of the plant against attack by undesirable phytopathogenic fungi and microorganisms and as microbicides for the direct control of phytopathogenic fungi and microorganisms. In addition, the compound (A) is also active against pests which damage plants (WO 99/24414). The activity of this substance is good; however, at low application rates it is in some cases unsatisfactory.

Furthermore, it is already known that neonicotinoids according to group (C) can be used for controlling pests of plant and crops (Pesticide Manual, 14th. Edition (2006); "Modern Agrochemicals", Vol. 4, No. 3, June 2005; EP-A 0 428 941) as well as the compounds of group (B) are also suitable for controlling pests of plants and crops (WO 2003/015519). However, the activity of these substances at low application rates is likewise not always sufficient. In addition, also the binary combinations of neonicotinoids according to group (C) and compounds from group (B) are known (WO 2003/015519; WO 2004/067528; WO 2005/107468; WO 2006/068669).

It is also known that the combination of Isotianil with neonicotinoids is suitable for controlling phytopathogenic fungi (WO 2005/009131).

Since, moreover, the environmental and economic requirements imposed on modern-day fungicides are continually increasing, with regard, for example, to the spectrum of action, toxicity, selectivity, application rate, formation of residues, and favorable preparation ability, and since, furthermore, there may be problems, for example, with resistances developing to known active compounds, a constant task is to develop new fungicide and insecticide agents which in some areas at least have advantages over their known counterparts.

The invention provides active compound combinations/compositions which in some aspects at least achieve the stated objectives.

It has now been found, surprisingly, that the combinations according to the invention not only bring about the additive enhancement of the spectrum of action with respect to the phytopathogenic fungi and/or microorganisms and/or pests to be controlled but achieve a synergistic effect which extends the range of action of the compound (A), (B) and (C) in two ways. Firstly, the rates of application of the compounds (A), (B) and (C) are lowered whilst the action remains equally good. Secondly, the combination still achieves a high degree of phytopathogen control even where the three individual compounds have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal and/or insecticidal activity, the combinations according to the invention also have further surprising advantageous properties which can also be described, in a wider sense, as synergistic activity. Examples of such advantageous properties that may be mentioned are: a broadening of the spectrum of fungicidal and/or insecticidal activity to other phytopathogenic fungi and/or microorganisms and/or pests, for example to resistant strains; a reduction in the rate of application of the active ingredients; adequate pest control with the aid of the compositions according to the invention, even at a rate of application at which the individual compounds are totally ineffective; advantageous behavior during formulation or upon application, for example upon grinding, sieving, emulsifying, dissolving or dispensing; increased storage stability; improved stability to light; more advantageous degradability; improved toxicological or ecotoxicological behavior; improved characteristics of the useful plants including: emergence, crop yields, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The combination according to the invention can also provide an improved systemicity to the active compounds that are used. Indeed, even if some of the used fungicide compound does not possess any or a satisfying systemicity, within the composition according to the invention these compounds can exhibit such a property.

In a similar manner, the combination according to the invention can allow an increased persistence of the fungicide efficacy of the active compounds that are employed.

Another advantage of the combination according to the invention relies in that an increased efficacy is achievable.

Accordingly, the present invention provides an active compound combination comprising (A) Isotianil and (B) a further insecticidal active compound selected from the group consisting of chlorantraniliprole (Cas No 500008-45-7) and 3-bromo-1-(3-chloropyridin-2-yl)-N-[4-cyano-2-methyl-6-(methylcarbamoyl)phenyl]-1H-pyrazole-5-carboxamide (Cas No. 736994-63-1).

Preferred preference is given to combinations comprising (A) Isotianil and (B) an insecticidal active compound chlorantraniliprole.

Preferred preference is given to combinations comprising compound (A) Isotianil and (B) an insecticidal active compound 3-bromo-1-(3-chloropyridin-2-yl)-N-[4-cyano-2-methyl-6-(methylcarbamoyl)phenyl]-1H-pyrazole-5-carboxamide.

In addition, the present invention provides an active compound combination comprising compound
(A) Isotianil and
(B) a further insecticidal active compound selected from the group consisting of chlorantraniliprole and 3-bromo-1-(3-chloropyridin-2-yl)-N-[4-cyano-2-methyl-6-(methylcarbamoyl)phenyl]-1H-pyrazole-1-carboxamide
(C) and a further insecticidal active compound selected from the group consisting of neonicotinoids, for example imidacloprid, acetamiprid, clothianidin, thiacloprid, thiamethoxam, imidaclothiz, nitenpyram, dinotefuran, and 1-[(2-chloro-5-thiazolyl)methyl]tetrahydro-3,5-dimethyl-N-nitro-1,3,5-triazin-2(1H)-imine.

Preference is given to combinations comprising (A) Isotianil and (B) chlorantraniliprole and (C) a further insecticidal active compound selected from the group consisting of neonicotinoids, for example imidacloprid, acetamiprid, clothianidin, thiacloprid, thiamethoxam, imidaclothiz, nitenpyram, dinotefuran, and 1-[(2-chloro-5-thiazolyl)methyl]tetrahydro-3,5-dimethyl-N-nitro-1,3,5-triazin-2(1H)-imine.

Preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carboxamide and (C) a further insecticidal active compound selected from the group consisting of neonicotinoids, for example imidacloprid, acetamiprid, clothianidin, thiacloprid, thiamethoxam, imidaclothiz, nitenpyram, dinotefuran, and 1-[(2-chloro-5-thiazolyl)methyl]tetrahydro-3,5-dimethyl-N-nitro-1,3,5-triazin-2(1H)-imine.

Preferred preference is given to combinations comprising compound (A) Isotianil and (B) chlorantraniliprole and (C) imidacloprid.

Preferred preference is given to combinations comprising compound (A) Isotianil- and (B) chlorantraniliprole and (C) acetamiprid.

Preferred preference is given to combinations comprising compound (A) Isotianil and (B) chlorantraniliprole and (C) clothianidin.

Preferred preference is given to combinations comprising compound (A) Isotianil and (B) chlorantraniliprole and (C) thiacloprid.

Preferred preference is given to combinations comprising compound (A) Isotianil and (B) chlorantraniliprole and (C) thiamethoxam.

Preferred preference is given to combinations comprising compound (A) Isotianil and (B) chlorantraniliprole and (C) imidaclothiz.

Preferred preference is given to combinations comprising compound (A) Isotianil and (B) chlorantraniliprole and (C) nitenpyram.

Preferred preference is given to combinations comprising compound (A) Isotianil and (B) chlorantraniliprole and (C) dinotefuran.

Preferred preference is given to combinations comprising compound (A) Isotianil and (B) chlorantraniliprole and (C) 1-[(2-chloro-5-thiazolyl)methyl]tetrahydro-3,5-dimethyl-N-nitro-1,3,5-triazin-2(1H)-imine.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carboxamide and (C) imidacloprid.

Preferred preference is given to combinations comprising compound (A) Isotianil and (B) 3-bromo-(3-chloropyridin-2-yl)-N-[4-cyano-2-methyl-6-(methylcarbamoyl)phenyl]-1H-pyrazole-5-carboxamide and (C) acetamiprid.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) clothianidin.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) thiacloprid.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) thiamethoxam.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) imidaclothiz.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazolo-5-carbox-amide and (C) nitenpyram.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) dinotefuran.

Preferred preference is given to combinations comprising compound (A) Isotianil and (B) 3-bromo-1-(3-chloropyridin-2-yl)-N-[4-cyano-2-methyl-6-(methylcarbamoyl)phenyl]-1H-pyrazole-5-carbox-amide and (C) 1-[(2-chloro-5-thiazolyl)methyl]tetrahydro-3,5-dimethyl-N-nitro-1,3,5-triazin-2(1H)-imine.

If the active compounds in the active compound binary combinations according to the invention are present in certain weight ratios, the synergistic effect is particularly pronounced. However, the weight ratios of the active compounds in the active compound combinations can be varied within a relatively wide range. In general, in the combinations according to the invention the compounds (A) and (B) are present in a synergistically effective weight ratio of (A):(B) in a range of 125:1 to 1:125, preferably in a weight ratio of 50:1 to 1:50, most preferably in a weight ratio of 20:1 to 1:20. In addition, the weight ratio between any two compounds, independently of each other, is from 1500:1 to 1:1500, preferably from 1250:1 to 1:1250, more preferably, 1000:1 to 1:1000 and most preferably 750:1 to 1:750. Further ratios of (A): (B) which can be used according to the present invention with increasing preference in the order given are: 900:1 to 1:900, 800:1 to 1:800, 700:1 to 1:700, 600:1 to 1:600, 500:1 to 1:500, 400:1 to 1:400, 300:1 to 1:300, 250:1 to 1:250, 200:1 to 1:200, 100:1 to 1:100, 90:1 to 1:90, 80:1 to 1:80, 70:1 to 1:70, 60:1 to 1:60, 40:1 to 1:40, 30:1 to 1:30, 10:1 to 1:10, 5:1 to 1:5, 4:1 to 1:4, 3:1 to 1:3.

For the ternary mixtures the weight ratio of active ingredient compounds is selected as to give the desired, for example synergistic, action. In general, the weight ratio would vary depending on the specific active compound. Generally the weight ratio between any two compounds, independently of each other, is from 125:1 to 1:125, preferably from 75:1 to 1:75, more preferably, 50:1 to 1:50 and most preferably 25:1 to 1:25. In addition, the weight ratio between any two compounds, independently of each other, is from 1500:1 to 1:1500, preferably from 1250:1 to 1:1250, more preferably, 1000:1 to 1:1000 and most preferably 750:1 to 1:750.

Further weight ratio between any two compounds, independently of each other, which can be used according to the present invention with increasing preference in the order given are 900:1 to 1:900, 800:1 to 1:800, 700:1 to 1:700, 600:1 to 1:600, 500:1 to 1:500, 400:1 to 1:400, 300:1 to 1:300, 250:1 to 1:250, 200:1 to 1:200, 100:1 to 1:100, 90:1 to 1:90, 80:1 to 1:80, 70:1 to 1:70, 60:1 to 1:60, 40:1 to 1:40, 30:1 to 1:30, 10:1 to 1:10, 5:1 to 1:5, 4:1 to 1:4, 3:1 to 1:3.

Where a compound (A), (B) or (C) can be present in tautomeric form, such a compound is understood hereinabove and herein below also to include, where applicable, corresponding tautomeric forms, even when these are not specifically mentioned in each case.

Compound (A), (B) or (C) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxy-carboxylic acids, e.g. ascorbic, lactic, malic, tartaric and citric acid, or benzoic acid, or with organic sulfonic acids, such as unsubstituted or substituted, e.g. halo-substituted, $C_1$-$C_4$ alkane- or aryl-sulfonic acids, e.g. methane- or p-toluene-sulfonic acid. Compounds (A) or compound (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propylamine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compound (A), (B) or (C) in free form and in the form of their salts, hereinabove and herein below any reference to the free compound (A), (B) or (C) or to their salts should be understood as including also the corresponding salts or the free compound (A), (B) or (C), respectively, where appropriate and expedient. The equivalent also applies to tautomers of compound (A), (B) or (C) and to their salts.

According to the invention the expression "combination" stands for the various combinations of compounds ((A) and (B)) or ((A) and (B) and (C)), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds ((A) and (B)) or ((A) and (B) and (C)) is not essential for working the present invention.

According to the invention the expression "pathogen" stands for all organisms which cause damages on plants or any part of a plant.

According to the invention the expression "fungi" stands for all fungal and chromista organisms.

According to the invention the expression "phytopathogenic fungi" stands for all fungal and chromista organisms which cause damages on plants or any part of a plant. Examples for fungal taxonomic groups are Ascomycota, Basidiomycota, Chytridiomycota, Deuteromycota, Glomeromycota, Microsporidia, Zygomycota, and anamorphic fungi. Examples for Chromista are Oomycota.

According to the invention the expression "microorganisms" stands for all bacterial and protozoan organisms. Examples are Plasmodiophoromycetes.

According to the invention the expression "viruses" stands for all viruses which cause damages on plants or any part of a plant. Examples are DNA-, RNA, and DNA and RNA reverse transcribing viruses as well as subviral agents.

According to the invention the expression "pests" stands for all aschelminthes and panarthropoda organisms which cause damages on plants or any part of a plant. Examples are Nematoda, Arthopoda, Hexapoda and Arachnida.

According to the invention the expression "insecticide" stands for the activity of a compound in combating unwanted insects, acari, or nematodes, or by reducing the damage of plants or plant parts by pests.

The active compounds within the composition according to the invention have potent microbicide activity and can be employed for controlling undesired phytopathogenic fungi and/or microorganisms and/or pests, in crop protection or in the protection of materials.

Within the composition according to the invention, fungicide compounds can be employed in crop protection for example for controlling phytopathogenic fungi and/or microorganisms such as Plasmodiophoromycetes, Oomycota, Chytridiomycota, Zygomycota, Ascomycota, Basidiomycota and Deuteromycota.

Within the composition according to the invention, bactericide compounds can be employed in crop protection for controlling microorganisms for example Pseudomonadaceae, Rhizobiaceae, Enterobacteriaceae, Corynebacteriaceae and Streptomycetaceae.

Within the composition according to the invention, insecticide compounds can be employed in crop protection for example for controlling pests such as lepidoptera.

The fungicidal and/or insecticidal combination and/or composition according to the invention can be used to curatively or preventively control the phytopathogenic fungi and/or microorganisms and/or pests of plants or crops. Thus, according to a further aspect of the invention, there is provided a method for curatively or preventively controlling the phytopathogenic fungi and/or microorganisms and/or pests of plants or crops comprising the use of a fungicide or insecticide composition according to the invention by application to the seed, the plant or to the fruit of the plant or to the soil in which the plant is growing or in which it is desired to grow.

According to the invention all plants and plant parts can be treated. By plants is meant all plants and plant populations such as desirable and undesirable wild plants, cultivars (including naturally occurring cultivars) and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods including transgenic plants.

By plant parts is meant all above ground and below ground parts and organs of plants such as shoot, leaf, flower, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

According to the invention the expression "plant propagation material" stands for all plant material which can be used either in the vegetative or generative reproduction of plants. Examples for plant propagation material are cuttings, corms, rhizomes, runners, seeds, fruits, grains, pods, fruiting bodies, tubers and seedlings.

The combination/composition according to the invention for combating phytopathogenic fungi and/or microorganisms and/or pests in crop protection comprises an effective, but not phytotoxic amount of the active compounds according to the invention. "Effective, but not phytotoxic amount" is defined as an amount of the combination according to the invention which is sufficient on one hand to control satisfactorily or completely eliminate the fungal disease of the plant and which on the other hand does not lead to any noteworthy symptoms of phytotoxicity. The effective dose can be varied in general in a larger range. The dose is dependent on several factors eg the fungi to be combatted, the plant, the climatic conditions, and on the active compounds of the combination according to the invention.

Among the plants that can be protected by the method according to the invention, mention may be made of major field crops like corn, soybean, cotton, *Brassica* oilseeds such as *Brassica napus* (e.g. canola). *Brassica rape, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rasaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliacea* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and lock), *Cruciferae* sp. (for instance white cabbage, red cabbage, broccoli, cauliflower, brussel sprouts, pak choi, kohlrabi, radish, horseradish, canola, rapeseed, mustard cress, Chinese cabbage, colza). *Leguminosae* sp. (for instance peanuts, peas and beans beans—such as climbing beans and broad beans), *Chenopodiaceae* sp. (for instance mangold, spinach beet, spinach, beetroots), *Asteraceae* sp. (for instance sunflower), *Papilionaceae* sp. (for instance soybean), *Malvaceae* (for instance okra), *Asparagaceae* (for instance asparagus); horticultural and forest crops; ornamental plants; as well as genetically modified homologues of those crops.

The method of treatment according to the invention is used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing ether gene(s) which are present in the plant (using for example, antisense technology, co-suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylamiocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is describe. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore at al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising pans of different insecticidal crystal proteins from *Bacillus thuringiensis* such as a hybrid of the proteins of 1) above or a hybrid of the proteins of 2) above, e.g., the Cry1A.105 protein produced by corn event MON98034; or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants b. plants which contain a stress tolerance enhancing transgene capable of reducing the expression and/or the activity of the PARG encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Examples of plants with the above-mentioned traits are non-exhaustively listed in Table A.

TABLE A

| No. | Effected target or expressed principle(s) | Crop phenotype/Tolerance to |
|---|---|---|
| A-1 | Acelolactate synthase (ALS) | Sulfonylureas, Imidazolinones, Triazolopyrimidines, Pyrimidyloxybenzoates, Phtalides |
| A-2 | AcetylCoA Carboxylase (ACCase) | Aryloxyphenoxyalkcanecarboxylic acids, cyclohexanediones |
| A-3 | Hydroxyphenylpyruvate dioxygenase (HPPD) | Isoxazoles such as Isoxaflutol or Isoxachlortol, Triones such as mesotrione or sulcotrione |
| A-4 | Phosphinothricin acetyltransferase | Phosphinothricin |
| A-5 | O-Methyl transferase | altered lignin levels |
| A-6 | Glutamtne synthetase | Glufosinate, Bialaphos |
| A-7 | Adenylosuccinate Lyase (ADSL) | Inhibitors of IMP and AMP synthesis |
| A-8 | Adenylosuccinate Synthase | Inhibitors of adenylosuccinate synthesis |
| A-9 | Anthranilate Synthase | Inhibitors of tryptophan synthesis and catabolism |
| A-10 | Nitrilase | 3,5-dihalo-4-hydroxy-benzonitriles such as Bromoxynil and Ioxinyl |
| A-11 | 5-Enolpyruvyl-3phosphoshikimate Synthase (EPSPS) | Glyphosate or sulfosate |
| A-12 | Glyphosate oxidoreductase | Glyphosate or sulfosate |
| A-13 | Protoporphyrinogen oxidase (PROTOX) | Diphenylethers, cyclic imides, phenylpyrazoles, pyridin derivatives, phenopylate, oxadiazoles, etc. |
| A-14 | Cytochrome P450 eg. P450 SU1 | Xenobiotics and herbicides such as Sulfonylureas |
| A-15 | Dimboa biosynthesis (Bxl gene) | *Helminthosporium turcicum, Rhopalosiphum maydis, Diplodia maydis, Ostrinia nubilalis, lepidoptera* sp. |
| A-16 | CMIII (small basic maize seed peptide) | plant pathogenes eg. *fusarium, alternaria, sclerotina* |
| A-17 | Corn-SAFP (zeamatin) | plant pathogenes eg. *fusarium, alternaria, sclerotina, rhizoctonia, chaetomium, phycomyces* |
| A-18 | Hml gene | Cochliobulus |
| A-19 | Chitinases | plant pathogenes |
| A-20 | Glucanases | plant pathogenes |
| A-21 | Coat proteins | viruses such as maize dwarf mosaic virus, maize chlorotic dwarf virus |
| A-22 | *Bacillus thuringiensis* toxins, VIP 3, *Bacillus cereus* toxins, *Photorabdus* and *Xenorhabdus* toxins | lepidoptera, coleoptera, diptera, nematodes, eg. *ostrinia nubilalis, heliothis zea*, armyworms eg. *Spodoptera frugiperda*, corn rootworms, *sesamia* sp., black cutworm, asian corn borer, weevils |
| A-23 | 3-Hydroxysteroid oxidase | lepidoptera, coleoptera, diptera, nematodes, eg. *ostrinia nubilalis, heliothis zea*, armyworms eg. *Spodoptera frugiperda*, corn rootworms, *sesamia* sp., black cutworm, asian corn borer, weevils |
| A-24 | Peroxidase | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-25 | Aminopeptidase inhibitors eg. Leucine aminopeptidase inhibitor (LAPI) | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-26 | Limonene synthase | corn rootworms |
| A-27 | Lectines | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-28 | Protease Inhibitors eg. cystatin, patatin, virgiferin, CPTI | weevils, corn rootworm |

TABLE A-continued

| No. | Effected target or expressed principle(s) | Crop phenotype/Tolerance to |
|---|---|---|
| A-29 | ribosome inactivating protein | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-30 | maize 5C9 polypeptide | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-31 | HMG-CoA reductase | lepidoptera, coleoptera, diptera, nematodes, eg. *ostrinia nubilalis, heliothis zea*, armyworms eg. *spodoptera frugiperda*, corn rootworms, *sesamia* sp., black cutworm, asian corn borer, weevils |
| A-32 | Inhibition of protein synthesis | Chloroactanilides such as Alachlor, Acetochlor, Dimethenamid |
| A-33 | Hormone mimic | 2,4-D, Mecoprop-P |

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan,
3) transgenic plants which produce hyaluronan.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

TABLE B

| | Petition | Extension of Petition Number *** | Institution | Regulated Article | Transgenic Phenotype | Transformation Event or Line | FR Notices | Preliminary EA **** or Risk Assessment | Final EA & Determination |
|---|---|---|---|---|---|---|---|---|---|
| B-1 | 07-253-01p | | Syngenta | Corn | | MIR-162 Maize | | | |
| B-2 | 07-180-01p | | Florigene | Carnation | Altered Flower Color | IFD-19890-1 & IFD-19907-9 | | | |
| B-3 | 07-152-01p | | Pioneer | Corn | glyphosate & Imidazolinone tolerant | HT-98140 | | | |
| B-4 | 07-108-01p | | Syngenta | Cotton | Lepidopteran Resistant | COT67B | | | |
| B-5 | 06-354-01p | | Pioneer | Soybean | High Oleic Acid | DP-305423-1 | | | |
| B-6 | 06-332-01p | | Bayer CropScience | Cotton | Glyphosate tolerant | GHB614 | | | |
| B-7 | 06-298-01p | | Monsanto | Corn | European Corn Borer resistant | MON 89034 | | | |
| B-8 | 06-271-01p | | Pioneer | Soybean | Glyphosate & acetolactate synthase tolerant | 356043 | 5-Oct-2007 | 06-271-01p_pea | |

TABLE B-continued

| Petition | Extension of Petition Number *** | Institution | Regulated Article | Transgenic Phenotype | Transformation Event or Line | FR Notices | Preliminary EA **** or Risk Assessment | Final EA & Determination |
|---|---|---|---|---|---|---|---|---|
| B-9 | 05-280-01p | | Syngenta | Corn | Thermostable alpha-amylase | 3272 | | | |
| B-10 | 04-337-01p | | University of Florida | Papaya | Papaya Ringspot Virus Resistant | X17-2 | | | |
| B-11 | 04-110-01p | | Monsanto & Forage Genetics | Alfalfa | Glyphosate Tolerant | J101, J163 | 23-Mar-2007; 27.06.2005; 03.02.2005; 24.11.2004 | 04-110-01p_pea | 04-110-01p_com |
| B-12 | 03-104-01p | | Monsanto & Scotts | Creeping bentgrass | Glyphosate Tolerant | ASR368 | Scoping & Status; 12-Oct-2005; 11.04.2005; 18.11.2004; 24.09.2004; 05.01.2004 | 03-104-01p_ra & CBG White Paper | |
| B-13 | 06-234-01p | 98-329-01p | Bayer CropScience | Rice | Phosphinothricin tolerant | LLRICE601 | 4-Dec-2006; 08.09.2006 | 06-234-01p_pea | 06-234-01p_com |
| B-14 | 06-178-01p | | Monsanto | Soybean | Glyphosate tolerant | MON 89788 | 02.08.2007; 05.02.2007 | 06-178-01p_pea | 06-178-01p_com |
| B-15 | 04-362-01p | | Syngenta | Corn | Corn Rootworm Protected | MIR604 | 23-Mar-2007; 22.02.2007; 10.01.2007 | 04-362-01p_pea | 04-362-01p_com |
| B-16 | 04-264-01p | | ARS | Plum | Plum Pox Virus Resistant | C5 | 13-July-2007; 16-May-2006 | 04-264-01p_pea | 04-264-01p_com |
| B-17 | 04-229-01p | | Monsanto | Corn | High Lysine | LY038 | 03.02.2006; 27.09.2005 | 04-229-01p_pea | 04-229-01p_com |
| B-18 | 04-125-01p | | Monsanto | Corn | Corn Rootworm Resistant | 88017 | 06.01.2006; 12.08.2005 | 04-125-01p_pea | 04-125-01p_com |
| B-19 | 04-086-01p | | Monsanto | Cotton | Glyphosate Tolerant | MON 88913 | 03.01.2005; 24.11.2004; 4-Oct-2004 | 04-086-01p_pea | 04-086-01p_com |
| B-20 | 03-353-01p | | Dow | Corn | Corn Rootworm Resistant | 59122 | 07.08.2005; 01.07.2005 | 03-353-01p_pea | 03-353-01p_com |
| B-21 | 03-323-01p | | Monsanto | Sugar Beet | Glyphosate Tolerant | H7-1 | 17-Mar-2005; 19-Oct-2004 | 03-323-01p_pea | 03-323-01p_com |
| B-22 | 03-181-01p | 00-136-01p | Dow | Corn | Lepidopteran Resistant & Phosphinothricin tolerant | TC-6275 | 01.11.2004; 17.08.2004 | 03-181-01p_pea | 03-181-01p_com |
| B-23 | 03-155-01p | | Syngenta | Cotton | Lepidopteran Resistant | COT 102 | 20.07.2005; 28.01.2005 | 03-155-01p_pea | 03-155-01p_com |
| B-24 | 03-036-01p | | Mycogen/Dow | Cotton | Lepidopteran Resistant | 281-24-236 | 13.08.2004; 9-Mar-2004 | 03-036-01p_pea | 03-036-01p_com |
| B-25 | 03-036-02p | | Mycogen/Dow | Cotton | Lepidopteran Resistant | 3006-210-23 | 13.08.20049-Mar-2004 | 03-036-02p_pea | 03-036-02p_com |
| B-26 | 02-042-01p | | Aventis | Cotton | Phosphinothericin tolerant | LLCotton25 | | | 02-042-01p_com |
| B-27 | 01-324-01p | 98-216-01p | Monsanto | Rapeseed | Glyphosate tolerant | RT200 | | | 01-324-01p_com |
| B-28 | 01-206-01p | 98-278-01p | Aventis | Rapeseed | Phosphinothricin tolerant & pollination control | MS1 & RF1/RF2 | | | 01-206-01p_com |
| B-29 | 01-206-02p | 97-205-01p | Aventis | Rapeseed | Phosphinothricin tolerant | Topas 19/2 | | | 01-206-02p_com |
| B-30 | 01-137-01p | | Monsanto | Corn | Corn Rootworm Resistant | MON 863 | | | 01-137-01p_com |
| B-31 | 01-121-01p | | Vector | Tobacco | Reduced nicotine | Vector 21-41 | | | 01-121-01p_com |
| B-32 | 00-342-01p | | Monsanto | Cotton | Lepidopteran resistant | Cotton Event 15985 | | | 00-342-01p_com |
| B-33 | 00-136-01p | | Mycogen c/o Dow & Pioneer | Corn | Lepidopteran resistant phosphinothricin tolerant | Line 1507 | | | 00-136-01p_com |
| B-34 | 00-011-01p | 97-099-01p | Monsanto | Corn | Glyphosate tolerant | NK603 | | | 00-011-01p_com |
| B-35 | 99-173-01p | 97-204-01p | Monsanto | Potato | PLRV & CPB resistant | RBMT22-82 | | | 99-173-01p_com |
| B-36 | 98-349-01p | 95-228-01p | AgrEvo | Corn | Phosphinothricin tolerant and Male sterile | MS6 | | | 98-349-01p_com |

TABLE B-continued

| | Petition | Extension of Petition Number *** | Institution | Regulated Article | Transgenic Phenotype | Transformation Event or Line | FR Notices | Preliminary EA **** or Risk Assessment | Final EA & Determination |
|---|---|---|---|---|---|---|---|---|---|
| B-37 | 98-335-01p | | U. of Saskatchewan | Flax | Tolerant to soil residues of sulfonyl urea herbicide | CDC Triffid | | | 98-335-01p_com |
| B-38 | 98-329-01p | | AgrEvo | Rice | Phosphinothricin tolerant | LLRICE06, LLRICE62 | | | 98-329-01p_com |
| B-39 | 98-278-01p | | AgrEvo | Rapeseed | Phosphinothricin tolerant & Pollination control | MS8 & RF3 | | | 98-278-01p_com |
| B-40 | 98-238-01p | | AgrEvo | Soybean | Phosphinothricin tolerant | GU262 | | | 98-238-01p_com |
| B-41 | 98-216-01p | | Monsanto | Rapeseed | Glyphosate tolerant | RT73 | | | 98-216-01p_com |
| B-42 | 98-173-01p | | Novartis Seeds & Monsanto | Beet | Glyphosate tolerant | GTSB77 | | | 98-173-01p_com |
| B-43 | 98-014-01p | 96-068-01p | AgrEvo | Soybean | Phosphinothricin tolerant | A5547-127 | | | 98-014-01p_com |
| B-44 | 97-342-01p | | Pioneer | Corn | Male sterile & Phosphinothricin tolerant | 676, 678, 680 | | | 97-342-01p_com |
| B-45 | 97-339-01p | | Monsanto | Potato | CPB & PVY resistant | RBMT15-101, SEMT15-02, SEMT15-15 | | | 97-339-01p_com |
| B-46 | 97-336-01p | | AgrEvo | Beet | Phosphinothricin tolerant | T-120-7 | | | 97-336-01p_com |
| B-47 | 97-287-01p | | Monsanto | Tomato | Lepidopteran resistant | 5345 | | | 97-287-01p_com |
| B-48 | 97-265-01p | | AgrEvo | Corn | Phosphinothricin tolerant & Lep. resistant | CBH-351 | | | 97-265-01p_com |
| B-49 | 97-205-01p | | AgrEvo | Rapeseed | Phosphinothricin tolerant | T45 | | | 97-205-01p_com |
| B-50 | 97-204-01p | | Monsanto | Potato | CPB & PLRV resistant | RBMT21-129 & RBMT21-350 | | | 97-204-01p_com |
| B-51 | 97-148-01p | | Bejo | *Cichorium intybus* | Male sterile | RM3-3, RM3-4, RM3-6 | | | 97-148-01p_com |
| B-52 | 97-099-01p | | Monsanto | Corn | Glyphosate tolerant | GA21 | | | 97-099-01p_com |
| B-53 | 97-013-01p | | Calgene | Cotton | Bromoxynil tolerant & Lepidopteran resistant | Events 31807 & 31808 | | | 97-013-01p_com |
| B-54 | 97-008-01p | | Du Pont | Soybean | Oil profile altered | G94-1, G94-19, G-168 | | | 97-008-01p_com |
| B-55 | 96-317-01p | | Monsanto | Corn | Glyphosate tolerant & ECB resistant | MON802 | | | 96-317-01p_com |
| B-56 | 96-291-01p | | DeKalb | Corn | European Corn Borer resistant | DBT418 | | | 96-291-01p_com |
| B-57 | 96-248-01p | 92-196-01p | Calgene | Tomato | Fruit ripening altered | 1 additional FLAVRSAVR line | | | 96-248-01p_com |
| B-58 | 96-068-01p | | AgrEvo | Soybean | Phosphinothricin tolerant | W62, W98, A2704-12, A2704-21, A5547-35 | | | 96-068-01p_com |
| B-59 | 96-051-01p | | Cornell U | Papaya | PRSV resistant | 55-1, 63-1 | | | 96-051-01p_com |
| B-60 | 96-017-01p | 95-093-01p | Monsanto | Corn | European Corn Borer resistant | MON809 & MON810 | | | 96-017-01p_com |
| B-61 | 95-352-01p | | Asgrow | Squash | CMV, ZYMV, WMV2 resistant | CZW-3 | | | 95-352-01p_com |
| B-62 | 95-338-01p | | Monsanto | Potato | CPB resistant | SBT02-5 & -7, ATBT04-6 &-27, -30, -31, -36 | | | 95-338-01p_com |
| B-63 | 95-324-01p | | Agritope | Tomato | Fruit ripening altered | 35 1 N | | | 95-324-01p_com |
| B-64 | 95-256-01p | | Du Pont | Cotton | Sulfonylurea tolerant | 19-51a | | | 95-256-01p_com |
| B-65 | 95-228-01p | | Plant Genetic Systems | Corn | Male sterile | MS3 | | | 95-228-01p_com |
| B-66 | 95-195-01p | | Northrup King | Corn | European Corn Borer resistant | Bt11 | | | 95-195-01p_com |
| B-67 | 95-179-01p | 92-196-01p | Calgene | Tomato | Fruit ripening altered | 2 additional FLAVRSAVR lines | | | 95-179-01p_com |

TABLE B-continued

| | Petition | Extension of Petition Number *** | Institution | Regulated Article | Transgenic Phenotype | Transformation Event or Line | FR Notices | Preliminary EA **** or Risk Assessment | Final EA & Determination |
|---|---|---|---|---|---|---|---|---|---|
| B-68 | 95-145-01p | | DeKalb | Corn | Phosphinothricin tolerant | B16 | | | 95-145-01p_com |
| B-69 | 95-093-01p | | Monsanto | Corn | Lepidopteran resistant | MON 80100 | | | 95-093-01p_com |
| B-70 | 95-053-01p | | Monsanto | Tomato | Fruit ripening altered | 8338 | | | 95-053-01p_com |
| B-71 | 95-045-01p | | Monsanto | Cotton | Glyphosate tolerant | 1445, 1698 | | | 95-045-01p_com |
| B-72 | 95-030-01p | 92-196-01p | Calgene | Tomato | Fruit ripening altered | 20 additional FLAVRSAVR lines | | | 95-030-01p_com |
| B-73 | 94-357-01p | | AgrEvo | Corn | Phosphinothricin tolerant | T14, T25 | | | 94-357-01p_com |
| B-74 | 94-319-01p | | Ciba Seeds | Corn | Lepidopteran resistant | Event 176 | | | 94-319-01p_com |
| B-75 | 94-308-01p | | Monsanto | Cotton | Lepidopteran resistant | 531, 757, 1076 | | | 94-308-01p_com |
| B-76 | 94-290-01p | | Zeneca & Petoseed | Tomato | Fruit polygalacturonase level decreased | B, Da, F | | | 94-290-01p_com |
| B-77 | 94-257-01p | | Monsanto | Potato | Coleopteran resistant | BT6, BT10, BT12, BT16, BT17, BT18, BT23 | 10-Mar-1995 | 94-257-01p_ea | 94-257-01p_com |
| B-78 | 94-230-01p | 92-196-01p | Calgene | Tomato | Fruit ripening altered | 9 additional FLAVRSAVR lines | | | 94-230-01p_com |
| B-79 | 94-228-01p | | DNA Plant Tech | Tomato | Fruit ripening altered | 1345-4 | 24. Jan 95 | 94-228-01p_ea | 94-228-01p_com |
| B-80 | 94-227-01p | 92-196-01p | Calgene | Tomato | Fruit ripening altered | Line N73 1436-111 | 3-Oct-1994 | | 94-227-01p_com |
| B-81 | 94-090-01p | | Calgene | Rapeseed | Oil profile altered | pCGN3828-212/86-18 & 23 | | | 94-090-01p_com |
| B-82 | 93-258-01p | | Monsanto | Soybean | Glyphosate tolerant | 40-3-2 | | | 93-258-01p_com |
| B-83 | 93-196-01p | | Calgene | Cotton | Bromoxynil tolerant | BXN | 22. Feb 94 | | 93-196-01p_com |
| B-84 | 92-204-01p | | Upjohn | Squash | WMV2 & ZYMV resistant | ZW-20 | 13-Dec-1994 | 92-204-01p_ea | 92-204-01p_com |
| B-85 | 92-196-01p | | Calgene | Tomato | Fruit ripening altered | FLAVRSAVR | 19-Oct-1992 | | 92-196-01p_com |

In a very particular embodiment a method for curatively or preventively controlling the phytopathogenic fungi and/or microorganisms and/or pests of plants or crops is described comprising the use of the combination of ((A) and (B)) or ((A) and (B) and (C)) by application to the seed, plant propagation material, the plant or to the fruit of genetically modified plants wherein the active principle expressed by the genetically modified plant corresponds to a line of table A or B.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or pests and/or viruses, the treated plants display a substantial degree of resistance to these phytopathogenic fungi and/or microorganisms and/or pests and/or viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

In a further aspect there is provided a composition comprising a combination according to this invention. Preferably the fungicidal and/or insecticidal composition comprises agriculturally acceptable additives, solvents, carriers surfactants, or extenders.

According to the invention, the term "carrier" denotes a natural or synthetic, organic or inorganic compound with which the active compound A of formula (I) and compound B are combined or associated to make it easier to apply, notably to the parts of the plant. This support is thus preferably inert and should be at least agriculturally acceptable. The support may be a solid or a liquid.

Suitable solid carriers are the following:
e.g. ammonium salts and natural rock powders, such as kaolins, clays, talcum, chalk, quartz, attapulgite, montmorillonite or diatomaceous earth and synthetic rock powders such as highly disperse silica, aluminium oxide and silicates, oil waxes, solid fertilizers, water, alcohols, preferably butanol, organic solvents, mineral and vegetable oils and derivatives thereof;

suitable solid carriers for granules are: for example crushed and fractionated natural rocks such as calcite, marble, pumice, sepiolite, dolomite and synthetic granules of inorganic and organic powders and granules of organic materials such as paper, sawdust, coconut shells, corn stalks and tobacco stalks;

By liquefied gaseous diluents or supports are meant such liquids that are gaseous at normal temperature and under normal pressure, for example, aerosol propellants such as halohydrocarbons as well as butane, propane, nitrogen and carbon dioxide.

It is possible to use in the formulations adhesives such as carboxymethylcellulose, natural and synthetic powdered, granular or latex-like polymers such as gum arabic, polyvinyl alcohol, polyvinyl acetate and natural phospholipids, such as cephalins and lecithins and synthetic phospholipids. Further additives can be mineral or vegetable oils and waxes, optionally modified.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkyl-naphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions, for example alkylaryl polyglycol ethers, alkyl sulphonates, alkyl sulphates, aryl sulphonates, protein hydrolyzates, lignosulphite waste liquors and methyl cellulose. The presence of at least one surfactant is generally essential when the active compound and/or the inert support are water-insoluble and when the vector agent for the application is water. Preferably, surfactant content may be comprised from 5% to 40% by weight of the composition.

Suitable emulsifiers and/or foam-forming agents are: for example non-ionic and anionic emulsifiers, such as polyoxyethylene fatty acid esters, polyoxyethylene fatty alcohol ethers, suitable dispersants are non-ionic and/or ionic substances, for example from the classes comprising alcohol POE and/or POP ethers, acid and/or POP or POE esters, alkyl-aryl and/or POP or POE ethers, fatty and/or POP-POE adducts, POE and/or POP polyol derivatives, POE and/or POP/sorbitan or sugar adducts, alkyl or azyl sulphates, sulphonates and phosphates or the corresponding PO ether adducts. Furthermore, suitable oligomers or polymers, for example based on vinyl monomers, acrylic acid, EO and/or PO alone or in combination with for example (poly-) alcohols or (poly-amines. Use can also be made of lignin and sulphonic acid derivatives thereof, simple and modified celluloses, aromatic and/or aliphatic sulphonic acids and adducts thereof with formaldehyde. Suitable as dispersants are for example lignosulphite waste liquors and methylcellulose.

Colouring agents such as inorganic pigments, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used.

Optionally, other additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compounds, preferably from 1 to 70% by weight, most preferably from 10 to 50% by weight.

The combination or composition according to the invention can be used as such, in form of their formulations or as the use forms prepared there from, such as aerosol dispenser, capsule suspension, cold fogging concentrate, hot fogging concentrate, encapsulated granule, fine granule, flowable concentrate for seed treatment, ready-to-use solutions, dustable powder, emulsifiable concentrate, emulsion oil in water, emulsion water in oil, macrogranule, microgranule, oil dispersible powder, oil miscible flowable concentrate, oil miscible liquid, froths, paste, seed coated with a pesticide, suspension concentrate (flowable concentrate), suspensions-emulsions-concentrates, soluble concentrate, suspensions, soluble powder, granule, water soluble granules or tablets, water soluble powder for seed treatment, wettable powder, natural and synthetic materials impregnated with active compound, micro-encapsulation in polymeric materials and in jackets for seed, as well as ULV-cold and hot fogging formulations, gas (under pressure), gas generating product, plant rodlet, powder for dry seed treatment, solution for seed treatment, ultra low volume (ULV) liquid, ultra low volume (ULV) suspension, water dispersible granules or tablets, water dispersible powder for slurry treatment.

These formulations are prepared in a known manner by mixing the active compounds or active compound combinations with customary additives, such as, for example, customary extenders and also solvents or diluents, emulsifiers, dispersants, and/or bonding or fixing agent, wetting agents, water repellents, if appropriate siccatives and UV stabilisers, colorants, pigments, defoamers, preservatives, secondary thickeners, adhesives, gibberellins and water as well further processing auxiliaries.

These compositions include not only compositions which are ready to be applied to the plant or seed to be treated by means of a suitable device, such as a spraying or dusting device, but also concentrated commercial compositions which must be diluted before application to the crop.

The control of phytopathogenic fungi and/or microorganisms and/or pests which damage plants post-emergence is carried out primarily by treating the soil and the above-ground parts of plants with crop protection agents. Owing to the concerns regarding a possible impact of crop protection agents on the environment and the health of humans and animals, there are efforts to reduce the amount of active compounds applied.

The active compound combinations according to the invention can be used in its commercially available formulations and in the use forms, prepared from these formulations, as a mixture with other active compounds, such as insecticides, attractants, sterilizing agents, bactericides, acaricides, nematicides, fungicides growth-regulating substances, herbicides, safeners, fertilizers or semiochemicals.

The treatment of plants and plant parts with the active compound combination according to the invention is carried out directly or by action on their environment, habitat or storage area by means of the normal treatment methods, for example by watering (drenching), drip irrigation, spraying, vaporizing, atomizing, broadcasting, dusting, foaming, spreading-on, and as a powder for dry seed treatment, a solution for seed treatment, a water-soluble powder for seed treatment, a water-soluble powder for slurry treatment, or by encrusting, in the case of propagation material, in particular in the case of seeds, furthermore by dry treatments, slurry treatments, liquid treatments, by one- or multi-layer coating. It is furthermore possible to apply the active compounds by the ultra-low volume method, or to inject the active compound preparation or the active compound itself into the soil.

The method of treatment according to the invention also provides the use of compounds ((A) and (B)) or ((A) and (B) and (C)) in a simultaneous, separate or sequential manner.

The dose of active compound/application rate usually applied in the method of treatment according to the invention is generally and advantageously
  for foliar treatments: from 0.1 to 10,000 g/ha, preferably from 10 to 1,000 g/ha, more preferably from 25 to 300 g/ha; in case of drench or drip application, the dose can even be reduced, especially while using inert substrates like rockwool or perlite;
  for seed treatment: from 2 to 200 g per 100 kilogram of seed, preferably from 3 to 150 g per 100 kilogram of seed;
  for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms and/or pests. The time range, in which protection is effected, spans in general one to 28 days, preferably one to 14 days after the treatment of the plants with the combinations or up to 200 days after the treatment of plant propagation material.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

A further aspect of the present invention is a method of protecting natural substances of vegetable or animal origin or their processed forms, which have been taken from the natural life cycle, which comprises applying to said natural substances of vegetable or animal origin or their processed forms a combination of compounds (A) and (B) in a synergistically effective amount.

A preferred embodiment is a method of protecting natural substances of vegetable origin or their processed forms, which have been taken from the natural life cycle, which comprises applying to said natural substances of vegetable origin or their processed forms a combination of compounds (A), (B) and (C) in a synergistically effective amount.

A further preferred embodiment is a method of protecting fruit, preferably pomes, stone fruits, soft fruits and citrus fruits, or their processed forms, which have been taken from the natural life cycle, which comprises applying to said natural substances of vegetable origin or their processed forms a combination of compounds (A) and (B) in a synergistically effective amount.

The invention comprises a procedure in which the seed is treated at the same time with a compound ((A) and (B)) or ((A) and (B) and (C)). It further comprises a method in which the seed is treated with compound ((A) and (B)) or ((A) and (B) and (C)) separately.

The invention also comprises a seed, which has been treated with a compound ((A) and (B)) or ((A) and (B) and (C)) at the same time. The invention also comprises a seed, which has been treated with a compound ((A) and (B)) or ((A) and (B) and (C)) separately. For the latter seed, the active ingredients can be applied in separate layers. These layers can optionally be separated by an additional layer that may or may not contain an active ingredient.

The combinations and/or compositions of the invention are particularly suitable for the treatment of seeds. A large part of the damage caused by pests and/or phytopathogenic fungi and/or microorganisms on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant. There is therefore considerable interest in protecting the seed and the germinating plant by the use of suitable agents.

The control of pests and/or phytopathogenic fungi and/or microorganisms by treatment of the seeds of plants has been known for a considerable time and is the object of continuous improvement. However, there are a number of problems in the treatment of seed that cannot always be satisfactorily solved. Therefore it is worthwhile to develop methods for the protection of seeds and germinating plants which makes the additional application of plant protection agents after seeding or after germination of the plants unnecessary. It is further worthwhile to optimize the amount of the applied active material such that the seed and the germinating plants are protected against infestation by pests and/or phytopathogenic fungi and/or microorganisms as best as possible without the plants themselves being damaged by the active compound applied. In particular, methods for the treatment seed should also take into account the intrinsic furgicidal and/or insecticidal properties of transgenic plants in order to achieve optimal protection of the seed and germinating plants with a minimal expenditure of plant protection agents.

The present invention relates therefore especially to a method for the protection of seed and germinating plants from infestation with pests and/or phytopathogenic fungi and/or microorganisms in that the seed is treated with the combination/composition of the invention. In addition the invention relates also to the use of the combination/composition of the invention for the treatment seed for protection of the seed and the germinating plants from pests and/or phytopathogenic fungi and/or microorganisms. Furthermore the invention relates to seed which was treated with a combination/composition of the invention for protection from pests and/or phytopathogenic fungi and/or microorganisms.

One of the advantages of the invention is because of the special systemic properties of the combination/composition of the invention treatment with this combination/composition protect not only the seed itself from pests and/or phytopathogenic fungi and/or microorganisms but also the plants emerging after sprouting. In this way the direct treatment of the culture at the time of sowing or shortly thereafter can be omitted.

A further advantage is the synergistic increase in fungicidal and/or insecticidal activity of the combination/composition of the invention in comparison to the respective individual active compounds, which extends beyond the sum of the activity of both individually applied active compounds. In this way an optimization of the amount of active compound applied is made possible.

It is also be regarded as advantageous that the mixtures of the invention can also be used in particular with transgenic seeds whereby the plants emerging from this seed are capable of the expression of a protein directed against pests and phytopathogenic fungi and/or microorganisms. By treatment of such seed with the agents of the invention certain pests and/or phytopathogenic fungi and/or microorganisms can already be controlled by expression of the, for example, insecticidal protein, and it is additionally surprising that a synergistic activity supplementation occurs with the agents of the invention, which improves still further the effectiveness of the protection from pest infestation.

The agents of the invention are suitable for the protection of seed of plant varieties of all types as already described which are used in agriculture, in greenhouses, in forestry, in furrow treatment, in horticulture or in vineyards. In particular, this concerns seed of cereals (like wheat, barley, rye, triticale, millet, oats, rice), maize, cotton, soya bean, potato, sunflower, beans, coffee, beet (e.g. sugar beet, mangold and feed beet), peanut, canola, rapeseed, poppy, olive, coconut, cacao, sugar cane or tobacco. The combination/compositions of the invention are also suitable for the treatment of the seed of fruit plants and vegetables (like tomato, cucumber, onion and lettuce), lawn, turf and ornamental plants as previously described. Particular importance is attached to the treatment of the seed of wheat, barley, rye, triticale, oats, maize, rice, soya bean, cotton, canola and rape.

As already described, the treatment of transgenic seed with a combination/composition of the invention is of particular importance. This concerns the seeds of plants which generally contain at least one heterologous gene that controls the expression of a polypeptide with special insecticidal properties. The heterologous gene in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed that contains at least one heterologous gene that originates from *Bacillus* sp. and whose gene product exhibits activity against the European corn borer and/or western corn rootworm. Particularly preferred is a heterologous gene that originates from *Bacillus thuringiensis*.

Within the context of the present invention the combination/composition of the invention is applied to the seed alone or in a suitable formulation. Preferably the seed is handled in a state in which it is so stable, that no damage occurs during treatment. In general treatment of the seed can be carried out at any time between harvest and sowing. Normally seed is used that was separated from the plant and has been freed of spadix, husks, stalks, pods, wool or fruit flesh. Use of seed that was harvested, purified, and dried to moisture content of below 15% w/w. Alternative, seed treated with water after drying and then dried again can also be used.

In general care must be taken during the treatment of the seed that the amount of the combination/composition of the invention and/or further additive applied to the seed is so chosen that the germination of the seed is not impaired and the emerging plant is not damaged. This is to be noted above all with active compounds which can show phytotoxic effects when applied in certain amounts.

The combination/compositions of the invention can be applied directly, that is without containing additional components and without being diluted. It is normally preferred to apply the combination/composition to the seed in the form of a suitable formulation. Suitable formulations and methods for seed treatment are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations and compositions which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and optionally water as well.

Suitable colorants that may be present in the seed dressing formulations of the invention include all colorants customary for such purposes. Use may be made both of pigments, of sparing solubility in water, and of dyes, which are soluble in water. Examples that may be mentioned include the colorants known under the designations rhodamine B, C.I. Pigment Red 112, and C.I. Solvent Red 1.

Suitable wetting agents that may be present in the seed dressing formulations of the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations of the invention include all nonionic, anionic, and cationic dispersants which are customary in the formulation of active agrochemical substances as outlined above.

Suitable defoamers that may be present in the seed dressing formulations of the invention include all foam-inhibiting substances which are customary in the formulation of active agrochemical substances. With preference it is possible to use silicone defoamers and magnesium stearate.

Suitable preservatives that may be present in the seed dressing formulations of the invention include all substances which can be used for such purposes in agrochemical compositions. By way of example, mention may be made of dichlorophen and benzyl alcohol hemiformal.

Suitable secondary thickeners that may be present in the seed dressing formulations of the invention include all substances which can be used for such purposes in agrochemical compositions. Preferred suitability is possessed by cellulose derivatives, acrylic acid derivatives, xanthan, modified clays, and highly dispersed silica.

Suitable adhesives that may be present in the seed dressing formulations of the invention include all customary binders which can be used in seed dressing. With preference, mention may be made of polyvinylpyrrolidone, polyvinyl acetate, polyvinyl alcohol and tylose.

Suitable gibberellins that may be present in the seed dressing formulations of the invention include preferably gibberelin A1, A3 (=gibberellinic acid), A4, and A7, particular preferably gibberelin A3 (=gibberellinic acid). The gibberellins of the formula (U) are known, the nomenclature of the gibberlins can be found the reference mentioned below (cf. R. Wegler "Chemie der Pflanzen-schutz- and Schädlingsbekämpfungsmittel", Volume 2, Springer Verlag, Berlin-Heidelberg-New York. 1970, pages 401-412).

Suitable mixing equipment for treating seed with the seed dressing formulations to be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compound combination, having good plant compatibility and favourable homeotherm toxicity, is suitable for controlling animal pests, in particular insects, arachnids and nematodes, encountered in agriculture, in forests, in the protection of stored products and materials and in the hygiene sector. It is preferably used as crop protection composition for foliar and soil treatment.

It is effective against normally sensitive and resistant species and against all or individual stages of development. The abovementioned pests include:

From the order of the Isopoda, for example, *Oniscus asellus, Armadillidium vulgare, Porcellio scaber*. From the order of the Diplopoda, for example, *Blaniulus guttulatus*. From the order of the Chilopoda, for example, *Geophilus carpophagus, Scutigera* spp. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Acheta domesticus, Gryllotalpa* spp., *Locusta migratoria* migratorioides, *Melanoplus* spp., *Schistocerca gregaria*. From the order of the Blattaria, for example, *Blatta orientalis, Periplaneta americana, Leucophaea maderae, Blattella germanica*. From the order of the Dermaptera, for example, *Forficula auricularia*. From the order of the Isoptera, for example, *Reticulitermes* app. From the order of the Phthiraptera, for example, *Pediculus humanus corporis, Haenmatopinus* spp., *Linognathus* spp., *Trichodectes* spp., *Damalinia* spp. From the order of the Thysanoptera, for example, *Hercinothrips femoralis, Thrips tabaci, Thrips palmi, Frankliniella occidentalis*. From the order of the Heteroptera, for example, *Eurygaster* spp., *Dysdercus intermedius, Piesma quadraa, Cimex lectularius, Rhodnius prolixus, Thiatoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Emnpoasca* spp., *Euscelis bilobatus, Nephotettix cincticeps, Lecanium corni, Saissetia oleae, Laodelphax striatellus, Nilaparvata lugens, Aonidiella aurarttii, Aspidiotus hederae, Pseudococcus* spp., *Psylla* spp. From the order of the Lepidoptera, for example, *Pectinophora gossypiela, Bupalus piniarius. Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phylloc-nistis citrella, Agrotis* spp., *Euxoa* spp., *Feltia* spp., *Earias insulana, Heliothis* spp., *Mamestra brassicae, Panolis flammea, Spodoptera* spp., *Tricboplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Metolontha melolontha, Amphimallon solstitialis, Costelytra zealandica, Lissorhoptrus oryzophilus*. From the order of the Hymenoptera, for example, *Diprion* spp., *Hoplocampa* spp., *Lasius* spp., *Monomorium pharaonis, Vespa* spp. From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannin* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp. From the order of the Siphonaptera, for example, *Xenopsylla cheopis, Ceratophyllus* spp. From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia practiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Triehodorus* spp., *Bursaphelenchus* spp.

Among the diseases of plants or crops that can be controlled by the method according to the invention mention may be made of:

Powdery Mildew diseases such as

*Blumeria* diseases caused for example by *Blumeria graminis*

*Podosphaera* diseases caused for example by *Podosphaera leucotricha*

*Sphaerotheca* diseases caused for example by *Sphaerotheca fuliginea*

*Uncinula* diseases caused for example by *Uncinula necator*

Rust diseases such as

*Gymnosporangium* diseases caused for example by *Gymnosporangium sabinae*

*Hemileia* diseases caused for example by *Hemileia vastatrix*

*Phakopsora* diseases caused for example by *Phakopsora pachyrhizi* and *Phakopsora meibomiae*
*Puccinia* diseases caused for example by *Puccinia recondite*, and *Puccinia triticina;*
*Uromyces* diseases caused for example by *Uromyces appendiculatus*
Oomycete diseases such as
*Bremia* diseases caused for example by *Bremia lactucae*
*Peronospora* diseases caused for example by *Peronospora pisi* and *Peronospora brassicae*
*Phytophthora* diseases caused for example by *Phytophthora infestans*
*Plasmopara* diseases caused for example by *Plasmopara viticola*
*Pseudoperonospora* diseases caused for example by *Pseudoperonospora humuli* and *Pseudoperonospora cubensis*
*Pythium* diseases caused for example by *Pythium ultimum*
Leafspot, Leaf blotch and Leaf blight diseases such as
*Alternaria* diseases caused for example by *Alternaria solani*
*Cercospora* diseases caused for example by *Cercospora beticola*
*Cladosporium* diseases caused for example by *Cladosporium cucumerinum*
*Cochliobolus* diseases caused for example by *Cochliobolus sativus*
(*Conidiaform: Drechslera*, Syn: *Helminthosporium*);
*Colletotrichum* diseases caused for example by *Colletotrichum lindemuthianum*
*Cycloconium* diseases caused for example by *Cycloconium oleaginum*
*Diaporthe* diseases caused for example by *Diaporthe citri*
*Elsinoe* diseases caused for example by *Elsinoe fawcettii*
*Gloeosporium* diseases caused for example by *Gloeosporium laeticolor*
*Glomerella* diseases caused for example by *Glomerella cingulata*
*Guignardia* diseases caused for example by *Guignardia bidwellii*
*Leptosphaeria* diseases caused for example by *Leptosphaeria maculans*
*Magnaporthe* diseases caused for example by *Magnaporthe grisea*
*Mycosphaerella* diseases caused for example by *Mycosphaerella graminicola* and *Mycosphaerella fijiensis*
*Phaeosphaeria* diseases caused for example by *Phaeosphaeria nodorum*
*Pyrenophora* diseases caused for example by *Pyrenophora teres*
*Ramularia* diseases caused for example by *Ramularia collocygni*
*Rhynchosporium* diseases caused for example by *Rhynchosporium secalis*
*Septoria* diseases caused for example by *Septoria apii;*
*Typhula* diseases caused for example by *Thyphula incarnata*
*Venturia* diseases caused for example by *Venturia inaequalis*
Root- and Stem diseases such as
*Corticium* diseases caused for example by *Corticium graminearum*
*Fusarium* diseases caused for example by *Fusarium oxysporum*
*Gaeumannomyces* diseases caused for example by *Gaeumannomyces graminis*
*Rhizoctonia* diseases caused for example by *Rhizoctonia solani*
*Oculimacula* (*Tapesia*) diseases caused for example by *Oculimacula Tapesia acuformis*

*Thielaviopsis* diseases caused for example by *Thielaviopsis basicola*
Ear and Panicle diseases including Maize cob such as
*Alternaria* diseases caused for example by *Alternaria* spp.
*Aspergillus* diseases caused for example by *Aspergillus flavus*
*Cladosporium* diseases caused for example by *Cladosporium cladosporioides*
*Claviceps* diseases caused for example by *Claviceps purpurea*
*Fusarium* diseases caused for example by *Fusarium culmorum*
*Gibberella* diseases caused for example by *Gibberella zeae*
*Monographella* diseases caused for example by *Monographella nivalis*
Smut- and Bunt diseases such as
*Sphacelotheca* diseases caused for example by *Sphacelotheca reiliana*
*Tilletia* diseases caused for example by *Tilletia caries*
*Urocystis* diseases *Urocystis occulta*
*Ustilago* diseases caused for example by *Ustilago nuda;*
Fruit Rot and Mould diseases such as
*Aspergillus* diseases caused for example by *Aspergillus flavus*
*Botrytis* diseases caused for example by *Botrytis cinerea*
*Penicillium* diseases caused for example by *Penicillium expansum* and *Penicillium purpurogenum*
*Sclerotinia* diseases caused for example by *Sclerotinia sclerotiorum;*
*Verticillium* diseases caused for example by *Verticillium alboatrum*
Seed- and Soilborne Decay, Mould, Wilt, Rot and Damping-off diseases
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus*
(As *conidia: Drechslera, Bipolaris* Syn: *Helminthosporium*);
*Colletotrichum* diseases, caused for example by *Colletotrichum coccodes;*
*Fusarium* diseases, caused for example by *Fusarium culmorum;*
*Gibberella* diseases, caused for example by *Gibberella zeae;*
*Macrophomina* diseases, caused for example by *Macrophomina phaseolina*
*Monographella* diseases, caused for example by *Monographella nivalis;*
*Penicillium* diseases, caused for example by *Penicillium expansum*
*Phoma* diseases, caused for example by *Phoma lingam*
*Phomopsis* diseases, caused for example by *Phomopsis sojae;*
*Phytophthora* diseases, caused for example by *Phytophthora cactorum;*
*Pyrenophora* diseases, caused for example by *Pyrenophora graminea*
*Pyricularia* diseases, caused for example by *Pyricularia oryzae;*
*Pythium* diseases, caused for example by *Pythium ultimum;*
*Rhizoctonia* diseases, caused for example by *Rhizoctonia solani;*
*Rhizopus* diseases, caused for example by *Rhizopus oryzae*

*Sclerotium* diseases, caused for example by *Sclerotium rolfsii*;
*Septoria* diseases, caused for example by *Septoria nodorum*;
*Typhula* diseases, caused for example by *Typhula incarnata*;
*Verticillium* diseases, caused for example by *Verticillium dahliae*
Canker, Broom and Dieback diseases such as
*Nectria* diseases caused for example by *Nectria galligena*
Blight diseases such as
*Monilinia* diseases caused for example by *Monilinia laxa*
Leaf Blister or Leaf Curl diseases including deformation of blooms and fruits such as
*Taphrina* diseases caused for example by *Taphrina deformans*
Decline diseases of wooden plants such as
*Esca* disease caused for example by *Phaeomoniella clamydospora* and *Phaeoacremonium aleophilum* and *Fomitiporia mediterranea*
Diseases of Flowers and Seeds such as
*Botrytis* diseases caused for example by *Botrytis cinerea*
Diseases of Tubers such as
*Rhizoctonia* diseases caused for example by *Rhizoctonia solani*
*Helminthosporium* diseases caused for example by *Helminthosporium solani*
Diseases caused by Bacterial Organisms such as
*Xanthomonas* species for example *Xanthomonas campestris* pv. *Oryzae*
*Pseudomonas* species for example *Pseudomonas syringae* pv. *Lachrymans*
*Erwinia* species for example *Erwinia amylovora*.
Fungal diseases of the foliage, upper stems, pods and seeds for example
*Alternaria* leaf spot (*Alternaria* spec. *atrans tenuissima*), Anthracnose (*Colletotrichum gloeosporoides dematium* var. *truncatum*), Brown spot (*Septoria glycines*), *Cercospora* leaf spot and blight (*Cercospora kikuchii*), *Choanephora* leaf blight (*Choanephora infundibulifera trispora* (Syn.)), *Dactuliophora* leaf spot (*Dactuliophora glycines*), Downy Mildew (*Peronospora manshurica*), *Drechslera* blight (*Drechslera glycini*), Frogeye Leaf spot (*Cercospora sojina*), *Leptosphaerulina* Leaf Spot (*Leptosphaerulina trifolii*), *Phyllostica* Leaf Spot (*Phyllosticta sojaecola*), Pod and Stem blight (*Phomopsis sojae*), Powdery Mildew (*Microsphaera diffusa*), *Pyrenochaeta* Leaf Spot (*Pyrenochaeta glycines*), Rhizoctonia Aerial, Foliage, and Web blight (*Rhizoctonia solani*), Rust (*Phakopsora pachyrhizi, Phakopsora meibomiae*), Scab (*Sphaceloma glycines*), *Stemphylium* Leaf blight (*Stemphylium botryosum*), Target Spot (*Corynespora cassiicola*)
Fungal disease of the Roots and Lower Stems for example Black Root Rot (*Calonectria crotalariae*), Charcoal Rot (*Macrophomina phaseolina*), Fusarium blight or Wilt, Root Rot, and Pod and Collar Rot (*Fusarium oxysporum, Fusarium orthoceras, Fusarium semitectum, Fusarium equiseti*), *Mycoleptodiscus* Root Rot (*Mycoleptodiscus terrestris*), *Neocosmospora* (*Neocosmospora vasinfecta*), Pod and Stem Blight (*Diaporthe phaseolorum*), Stem Canker (*Diaporthe phaseolorum* var. *caulivora*), *Phytophthora* Rot (*Phytophthora megasperma*), Brown Stem Rot (*Phialophora gregata*), *Pythium* Rot (*Pythium aphanidermatum, Pythium irregulare, Pythium debaryanum, Pythium myriotylum, Pythium ultimum*), *Rhizoctonia* Root Rot, Stem Decay, and Damping-Off (*Rhizoctonia solani*), *Sclerotinia* Stem Decay (*Sclerotinia sclerotiorum*), *Sclerotinia* Southern Blight (*Sclerotinia rolfsii*), *Thielaviopsis* Root Rot (*Thielaviopsis basicola*).

Furthermore combinations and compositions according to the invention may also be used to reduce the contents of mycotoxins in plants and the harvested plant material and therefore in foods and animal feed stuff made therefrom.

Especially but not exclusively the following mycotoxins can be specified:
Deoxynivalenole (DON), Nivalenole, 15-Ac-DON, 3-Ac-DON, 12- and HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxines, which are caused for example by the following fungal diseases: *Fusariumn* spec., like *Fusarium acuminatum, F. avenaceum, F. crookwelense, F. culmorum, F. graminearum* (*Gibberella zeae*), *F. equiseti, F. fujikoroi, F. musarum, F. oxysporum, F. proliferatum, F. poae, F. pseudograminearunm, F. sambucinum, F. scirpi, F. semitectun, F. solani, F. sporotrichoides, F. langsethiae, F. subglutinans, F. tricinctum, F. verticillioides* and others but also by *Aspergillus* spec., *Penicillium* spec. *Claviceps purpurea, Stachybotrys* spec. and others.

The very good fungicidal effect of the combinations or compositions according to the invention is shown in the following example. While the single active compounds do show weaknesses in their fungicidal efficacy, the combinations or compositions show an effect which is greater than the single addition of the efficacies of each compound.

A synergistic effect does always exist for fungicides, if the fungicidal efficacy of the combinations or compositions according to the invention is greater than the expected efficacy for the combination of two active compounds according to S. R. Colby ("Calculation of the synergistic and antagonistic responses of herbicide combinations" Weeds, (1967), 15, pages 20-22) which is calculated as shown below:
If
X is the efficacy observed for compound (A) at a defined dose (m g/ha or m ppm),
Y is the efficacy observed for compound (B) at a defined dose (n g/ha or n ppm),
E is the efficacy observed for compound (A) and compound (B) together at defined doses of m and a g/ha or m and n ppm,
the Colby formula can be defined as shown below $$E_1 = X + Y - \frac{X \cdot Y}{100}.$$

The efficacies are calculated as %. 0% efficacy is corresponding to the non-treated, fully infected control, while an efficacy of 100% implies that no infection at all can be observed.

In case that the fungicidal effect actual observed is greater than the efficacy calculated using Colby's formula, the combinations or compositions are superadditive, i.e. a synergistic effect can be observed.

The term "synergistic effect" also means the effect defined by application of the Tammes method, "Isoboles, a graphic representation of synergism in pesticides", Netherlands Journal of Plant Pathology, 70 (1964), pages 73-80.

The invention is illustrated by the example below. The invention is not restricted to the example only.

The very good fungicidal and/or insecticidal effect of the combinations or compositions according to the invention is shown in the following example. While the single active compounds do show weaknesses in their fungicidal or insecticidal efficacy, the combinations or compositions show an effect which is greater than the single addition of the efficacies of each compound.

A synergistic effect does exist for fungicides or insecticides, if the fungicidal or insecticidal efficacy of the combinations or compositions according to the invention is greater than the expected efficacy for the combination of three active compounds according to S. R. Colby ("Calculation of the synergistic and antagonistic responses of herbicide combinations" Weeds, (1967), 15, pages 20-22) which is calculated as shown below:

If

X is the efficacy observed for compound (A) at a defined dose (m g/ha or m ppm), Y is the efficacy observed for compound (B) at a defined dose (n g/ha or n ppm), Z is the efficacy observed for compound (C) at a defined dose (r g/ha or r ppm), E is the efficacy observed for compound (A) and compound (B) and compound (C) together at defined doses of m, n and r g/ha or m, n and r ppm, the Colby formula can be defined as shown below $$E = X + Y + Z - \frac{X*Y + Y*Z + X*Z}{100} + \frac{X*Y*Z}{10000}.$$

The efficacies are calculated as %. 0% efficacy is corresponding to the non-treated, fully infected control, while an efficacy of 100% implies that no infection at all can be observed.

In case that the fungicidal effect actual observed is greater than the additive efficacy calculated using Colby's formula, the combinations or compositions are superadditive, i.e. a synergistic effect can be observed.

The term "synergistic effect" also means the effect defined by application of the Tammes method. "Isoboles, a graphic representation of synergism in pesticides", Netherlands Journal of Plant Pathology, 70 (1964), pages 73-80.

The invention is illustrated by the example below. The invention is not restricted to the example only.

The good fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20-22, 1967):

If

X is the efficacy, when applying the active compound A at a rate of application of active compound of m g/ha, Y is the efficacy, when applying the active compound B at a rate of application of active compound of a g/ha, E is the expected efficacy, when applying the active compounds A and B at rates of application of active compound of m and n g/ha, then $$E = X + Y - \frac{X \cdot Y}{100}.$$

The degree of efficacy, expressed in % is denoted. 0% means an efficacy which corresponds to that of the control while an efficacy of 100% means that no disease is observed.

If the actual fungicidal activity exceeds the calculated value, then die activity of the combination is superadditive, i.e. a synergistic effect exists. In this case, the efficacy which was actually observed must be greater than the value for the expected efficacy (E) calculated from the above-mentioned formula.

The invention is illustrated by the following examples.

EXAMPLE A

*Blumeria* Test (Barley) SAR 5d

Solvent: 50 parts by weight of n,n-dimethylacetamid

Emulsifier: 1 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for systemic activated resistance, young plants are sprayed with the preparation of active compound or active compound combination at the stated rate of application. After the spray coating has dried on, the plants are placed in a greenhouse at a temperature of approximately 18° C. and a relative atmospheric humidity of approximately 80%.

5 days after spraying, the plants are dusted with spores of *Blumeria graminis* f. sp. *hordei*. The plants then remain in a greenhouse at a temperature of approximately 18° C. and a relative atmospheric humidity of approximately 80% to promote the development of mildew pustules.

The test is evaluated 7 days after the inoculation, 1. and 2. leaf separated. 0% means an efficacy with corresponds to that of the control while an efficacy of 100% means that no disease is observed.

The table below clearly shows that the observed activity of the active compound combination according to the invention is greater than the calculated activity, i.e. a synergistic effect is present.

TABLE A-1

Blumeria test (barley)/SAR 5d
$1^{st}$ leaf

| Active compound Known: | Rate of application of active compound in ppm | Efficacy in % |
|---|---|---|
| Isotianil | 1000 | 44 |

TABLE A-1-continued

Blumeria test (barley)/SAR 5d
1st leaf

| Active compound Known: | Rate of application of active compound in ppm | Efficacy in % |
|---|---|---|
| Chlorantraniliprole | 1000 | 11 |

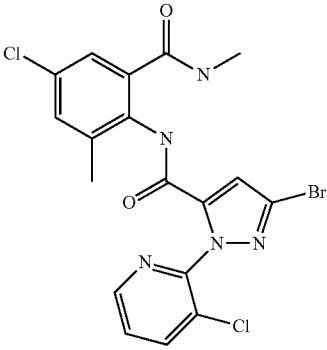

Inventive Compound Combination:

| | Ratio of the mixture | Rate of application of active compound in ppm | Actual efficacy | Expected value, calculated using Colby's formula |
|---|---|---|---|---|
| Isotianil + Chlorantraniliprole | 1:1 | 1000 + 1000 | 56 | 50 |

TABLE A-2

Blumeria test (barley)/SAR 5d
1st leaf

| Active compound Known: | Rate of application of active compound in ppm | Efficacy in % |
|---|---|---|
| Isotianil | 1000 | 44 |

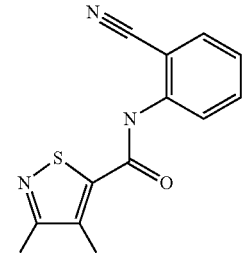

TABLE A-2-continued

Blumeria test (barley)/SAR 5d
1st leaf

| Active compound Known: | Rate of application of active compound in ppm | Efficacy in % |
|---|---|---|
| Chlorantraniliprole | 1000 | 0 |

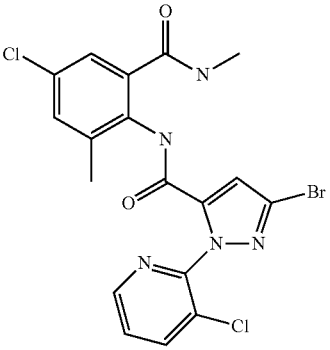

Inventive Compound Combination:

| | Ratio of the mixture | Rate of application of active compound in ppm | Actual efficacy | Expected value, calculated using Colby's formula |
|---|---|---|---|---|
| Isotianil + Chlorantraniliprole | 1:1 | 1000 + 1000 | 56 | 44 |

Formula for the Efficacy of the Combination of Two or Three Compounds

The expected efficacy of a given combination of two compounds is calculated as follows (see Colby, S. R., "Calculating Synergistic and antagonistic Responses of Herbicide Combinations", Weeds 15, pp. 20-22, 1967):

If

X is the efficacy expressed in % mortality of the untreated control for test compound A at a concentration of m ppm respectively m g/ha, Y is the efficacy expressed in % mortality of the untreated control for test compound B at a concentration of n ppm respectively a g/ha, Z is the efficacy expressed in % mortality of the untreated control for test compound C at a concentration of g ppm respectively g g/ha, E is the efficacy expressed in % mortality of the untreated control using the mixture of A, B and C at m, n and o ppm respectively m, n and o g/ha, then is $$E = X + Y + Z - \frac{XY + YZ + XZ}{100} + \frac{XYZ}{10000}$$

If the observed insecticidal efficacy of the combination is higher than the one calculated as "E", then the combination of the two compounds is more than additive, i.e., there is a synergistic effect.

EXAMPLE B

Nilaparvata lugens-Test

Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Rice plants (*Oryza sativa*) are treated by being sprayed with the preparation of the active compound at the desired concentration and are infested with larvae of the Brown plant hopper (*Nilaparvata lugens*) as long as the leaves are still moist.

After the specified period of time, the mortality in % is determined. 100% means that all the hopper larvae have been killed; 0% means that none of the hopper larvae have been killed.

According to the present application in this test e.g. the following combination shows a synergistic effect in comparison to the single compounds:

TABLE B

Nilaparvata lugens-test

| Active Ingredient | Concentration in ppm | Efficacy in % after $3^d$ | |
|---|---|---|---|
| Isotianil | 200 | 0 | |
| Chlorantraniliprole | 4 | 0 | |
| Clothianidin | 4 | 90 | |
| Isotianil + Chloranthraniliprole + Clothianidin (50:1:1) according to the invention | 200 + 4 + 4 | obs. * 100 | cal. ** 90 |

* obs. = observed insecticidal efficacy
** cal. = efficacy calculated with Colby-formula

EXAMPLE C

Phaedon cochleariae-Test

Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being sprayed with the preparation of the active compound at the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

According to the present application in this test e.g. the following combination shows a synergistic effect in comparison to the single compounds:

TABLE C-1

Phaedon cochleariae-Test (3 day evaluation)

| Active ingredient | Concentration in ppm | Efficacy in % after $3^d$ | |
|---|---|---|---|
| Isotianil | 200 | 0 | |
| Chlorantraniliprole | 0.16 | 0 | |
| Imidacloprid | 4 | 0 | |
| Isotianil + Chlorthraniliprole + Imidacloprid (1250:1:25) according to the invention | 200 + 0.16 + 4 | obs. * 70 | cal. ** 0 |

* obs. = observed insecticidal efficacy
** cal. = efficacy calculated with Colby-formula

TABLE C-2

Phaedon cochleariae-test (4 day evaluation)

| Active Ingredient | Concentration in ppm | Efficacy in % after $4^d$ | |
|---|---|---|---|
| Isotianil | 200 | 15 | |
| Chlorantraniliprole | 4 | 70 | |
|  | 0.8 | 45 | |
| Clothianidin | 20 | 70 | |
| Isotianil + Chloranthraniliprole + Clothianidin (50:1:5) according to the invention | 200 + 4 + 20 | obs. * 95 | cal. ** 77.65 |
| Thiacloprid | 4 | 45 | |
| Isotianil + Chloranthraniliprole + Thiacloprid (250:1:5) according to the invention | 200 + 0.8 + 4 | obs. * 100 | cal. ** 74.29 |

* obs. = observed insecticidal efficacy
** cal. = efficacy calculated with Colby-formula

TABLE C-3

Phaedon cochleariae-test (6 day evaluation)

| Active Ingredient | Concentration in ppm | Efficacy in % after $6^d$ | |
|---|---|---|---|
| Isotianil | 200 | 0 | |
| Chlorantraniliprole | 0.8 | 15 | |
| Isotianil + Chloranthraniliprole (250:1) according to the invention | 200 + 0.8 | obs. * 45 | cal. ** 15 |
| Clothianidin | 4 | 90 | |
| Isotianil + Chloranthraniliprole + Clothianidin (50:1:1) according to the invention | 200 + 4 + 4 | obs. * 100 | cal. ** 90 |

* obs. = observed insecticidal efficacy
** cal. = efficacy calculated with Colby-formula

EXAMPLE D

Spodoptera frugiperda Test

Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being sprayed into the preparation of the active compound of the desired concentration and are infested with larvae of the fall army worm (*Spodoptera frugiperda*) as long as the leaves are still moist.

After the specified period of time, the mortality in % is determined. 100% means that all the caterpillars have been killed; 0% means that none of the caterpillars have been killed.

According to the present application in this test e.g. the following combination shows a synergistic effect in comparison to the single compounds:

TABLE D

*Spodoptera frogiperda*-Test

| Active Ingredient | Concentration in ppm | Efficacy in % after 6$^d$ |
|---|---|---|
| Isotianil | 200 | 0 |
| Chlorantraniliprole | 0.032 | 15 |
| Acetamiprid | 0.16 | 15 |
| Isotianil + Chloranthraniliprole + Acetamiprid (6250:1:5) according to the invention | 200 + 0.032 + 0.16 | obs. * 50  cal. ** 27.75 |

\* obs. = observed insecticidal efficacy
\*\* cal. = efficacy calculated with Colby-formula

EXAMPLE E

*Pyricularia* Test (Rice)/Protective 1d

Solvent: 28.5 parts by weight of acetone
Emulsifier: 1.5 parts by weight of polyoxyethylene alkyl phenyl ether To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound or active compound combination at the stated rate of application. After the spray coating has dried on, the plants are placed in a greenhouse at a temperature of approximately 23° C. and a relative atmospheric humidity of approximately 70%.

1 day after spraying, the plants are inoculated with an aqueous spore suspension of the causal agent of rice blast (*Pyricularia oryzae*). The plants are then placed in an incubator at approximately 25° C. and a relative atmospheric humidity of approximately 100% for 1 day.

The test is evaluated 5 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

TABLE E

*Pyricularia* test (rice)/protective 1d

| Active compound Known: | Rate of application of active compound in ppm | Efficacy in % |
|---|---|---|
| (I) Isotianil | 20 | 35 |
| (II) Chlorantraniliprole | 20 | 0 |
| (III) Imidacloprid | 20 | 0 |

Inventive Compound Combination:

| | Ratio of the mixture | Rate of application of active compound in ppm | Actual efficacy | Expected value, calculated using Colby's formula |
|---|---|---|---|---|
| (I) Isotianil + (II) Chlorantraniliprole + (III) Imidacloprid | 1:1:1 | 20 + 20 + 20 | 60 | 35 |

EXAMPLE F

*Pyricularla* Test (Rice)/SAR 5d

Solvent: 28.5 parts by weight of acetone
Emulsifier: 1.5 parts by weight of polyoxyethylene alkyl phenyl ether To produce a suitable preparation of active compound, 1 part by weight of active compound or active compound combination is mixed with the stated amounts of solvent and emulsifier, and the concentrate is diluted with water to the desired concentration.

To test for systemic activated resistance, young plants are sprayed with the preparation of active compound or active compound combination at the stated rate of application. After the spray coating has dried on, the plants are placed in a greenhouse at a temperature of approximately 23° C. and a relative atmospheric humidity of approximately 70%.

5 days after spraying, the plants are inoculated with an aqueous spare suspension of the causal agent of rice blast (*Pyricularla oryzae*). The plants are then placed in an incubator at approximately 25° C. and a relative atmospheric humidity of approximately 100% for 1 day.

The test is evaluated 7 days after the inoculation. 0% means an efficacy which corresponds to that of the control, while an efficacy of 100% means that no disease is observed.

The table below clearly shows that the observed activity of the active compound combination according to the invention is greater than the calculated activity, i.e. a synergistic effect is present.

TABLE F

*Pyricularia* test (rice)/SAR 5d

| Active compound Known: | Rate of application of active compound in ppm | Efficacy in % |
|---|---|---|
| (I) Isotianil | 100 | 43 |
| (II) Chlorantraniliprole | 100 | 0 |
| (III) Imidacloprid | 100 | 0 |

Inventive Compound Combination:

| | Ratio of the mixture | Rate of application of active compound in ppm | Actual efficacy | Expected value, calculated using Colby's formula |
|---|---|---|---|---|
| (I) Isotianil + (II) Chlorantraniliprole + (III) Imidacloprid | 1:1:1 | 100 + 100 + 100 | 80 | 43 |

The invention claimed is:

1. A composition comprising
   (A) Isotianil and
   (B) a first insecticidal active compound selected from the group consisting of chlorantraniliprole and 3-bromo-1-(3-chloropyridin-2-yl)-N-[4-cyano-2-methyl-6-(methylcarbamoyl)phenyl]-1H-pyrazole-5-carboxamide; and
   (C) thiamethoxam.

2. The composition according to claim 1 wherein the weight ratio between any two components (A), (B), or (C), independently of each other, is 1:1250 to 1250:1.

3. The composition according to claim 1, further comprising adjuvants, solvents, carriers, surfactants or extenders.

4. A method for curatively or preventively controlling phytopathogenic fungi, microorganisms, or pests of plants or crops comprising applying:
   (A) Isotianil;
   (B) a first insecticidal active compound selected from the group consisting of chlorantraniliprole and 3-bromo-1-(3-chloropyridin-2-yl)-N-[4-cyano-2-methyl-6-(methylcarbamoyl)phenyl]-1H-pyrazole-5-carboxamide; and
   (C) thiamethoxam, to a seed, to plant propagation material, to a plant, to fruit of a plant, to soil in which the plant is growing, or to soil from which a seed, a plant propagation material, or a plant grows.

5. The method according to claim 4, comprising applying:
   (A) Isotianil;
   (B) the first insecticidal active compound; and
   (C) thiamethoxam, separately, simultaneously, or sequentially.

6. The method according to claim 4 wherein
   (A) Isotianil;
   (B) the first insecticidal active compound; and
   (C) thiamethoxam, are applied at a rate of from 0.1 g/ha to 10 kg/ha for foliar treatment; are applied at a rate of from 0.1 g/ha to 10 kg/ha for soil treatment; or are applied at a rate of from 2 to 200 g/100 kg of seed for seed treatment.

7. A method for protecting a seed, shoots, foliage, or combinations thereof of a plant grown from a seed from damage by a pest or a fungus comprising treating an unsown seed with
   (A) Isotianil;
   (B) a first insecticidal active compound selected from the group consisting of chlorantraniliprole and 3-bromo-1-(3-chloropyridin-2-yl)-N-[4-cyano-2-methyl-6-(methylcarbamoyl)phenyl]-1H-pyrazole-5-carboxamide; and
   (C) thiamethoxam.

8. The method according to claim 7, wherein the unsown seed is treated at the same time, sequentially, or separately with
   (A) Isotianil;
   (B) the first insecticidal active compound; and
   (C) thiamethoxam.

9. A composition comprising:
   seed;
   (A) Isotianil;
   (B) a first insecticidal active compound selected from the group consisting of chlorantraniliprole and 3-bromo-1-(3-chloropyridin-2-yl)-N-[4-cyano-2-methyl-6-(methylcarbamoyl)phenyl]-1H-pyrazole-5-carboxamide; and
   (C) thiamethoxam.

\* \* \* \* \*